US00PP26066P3

(12) United States Plant Patent
Van Rosmalen

(10) Patent No.: US PP26,066 P3
(45) Date of Patent: Nov. 10, 2015

(54) *PHALAENOPSIS* ORCHID PLANT NAMED 'PHALDONFI'

(50) Latin Name: ***Phalaenopsis* hybrid**
Varietal Denomination: Phaldonfi

(71) Applicant: ANTHURA B.V., Bleiswijk (NL)

(72) Inventor: Nicolaas Arnoldus Maria Van Rosmalen, Velp (NL)

(73) Assignee: ANTHURA B.V., Bleiswijk (NL)

( * ) Notice: Subject to any disclaimer, the term of this patent is extended or adjusted under 35 U.S.C. 154(b) by 181 days.

(21) Appl. No.: 13/987,570

(22) Filed: Aug. 8, 2013

(65) Prior Publication Data

US 2015/0047084 P1 Feb. 12, 2015

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

Anthura Unlimited in Varieties Phalaenopsis Pot Plant Culture 2012, pp. 1-52.*
Anthura Phalaenopsis: Cut flower and pot plant culture, 2012, pp. 1 and 51.
Anthura Phalaenopsis: Pot plant culture, 2014, pp. 1 and 51.

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named PHALDONFI', particularly characterized by light pink flowers with purple stripes and red lip, 2 to 3 peduncles, a short and sturdy inflorescence, a narrow oblong leaf shape, and propagated by tissue culture is disclosed.

3 Drawing Sheets

Genus and species: *Phalaenopsis* hybrid.
Variety denomination: 'PHALDONFI'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDONFI'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* PHALDONFI' is particularly characterized by its attractive and unique pink flowers, economical propagation by tissue culture, rapid growth, and a plant dimension suitable for packaging and shipping to the market.

'PHALDONFI' is a product of a planned breeding program conducted in Bleiswijk, The Netherlands.

The new *Phalaenopsis* 'PHALDONFI' originated from a cross made in February 2003 in Bleiswijk, The Netherlands. The female parent is a pink *Phalaenopsis* pot plant name '01-0269' (unpatented), while the male parent is a pink *Phalaenopsis* pot plant named '01-1464' (unpatented). A single plant was selected in May 2007 and has been asexually reproduced repeatedly by meristem tissue culture in Bleiswijk, The Netherlands over a 6-year period. The new variety has been found to retain its distinctive characteristics through successive asexual propagations.

Asexual reproduction of 'PHALDONFI' by meristem tissue culture was first performed in April 2010 in Bleiswijk, The Netherlands and has demonstrated that the new cultivar is firmly fixed and retained through successive generations of asexual reproduction.

Plant Breeder's Rights for this variety have been applied for in Europe on January 15, 2013. 'PHALDONFI' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Light pink flower with purple stripes and red lip;
2) 2 to 3 peduncles;

3) Inflorescence is short and sturdy;
4) The shape of the leaf is narrow oblong; and
5) Plants are propagated by tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in April 2013.

DESCRIPTION OF THE NEW VARIETY

Figure 1:
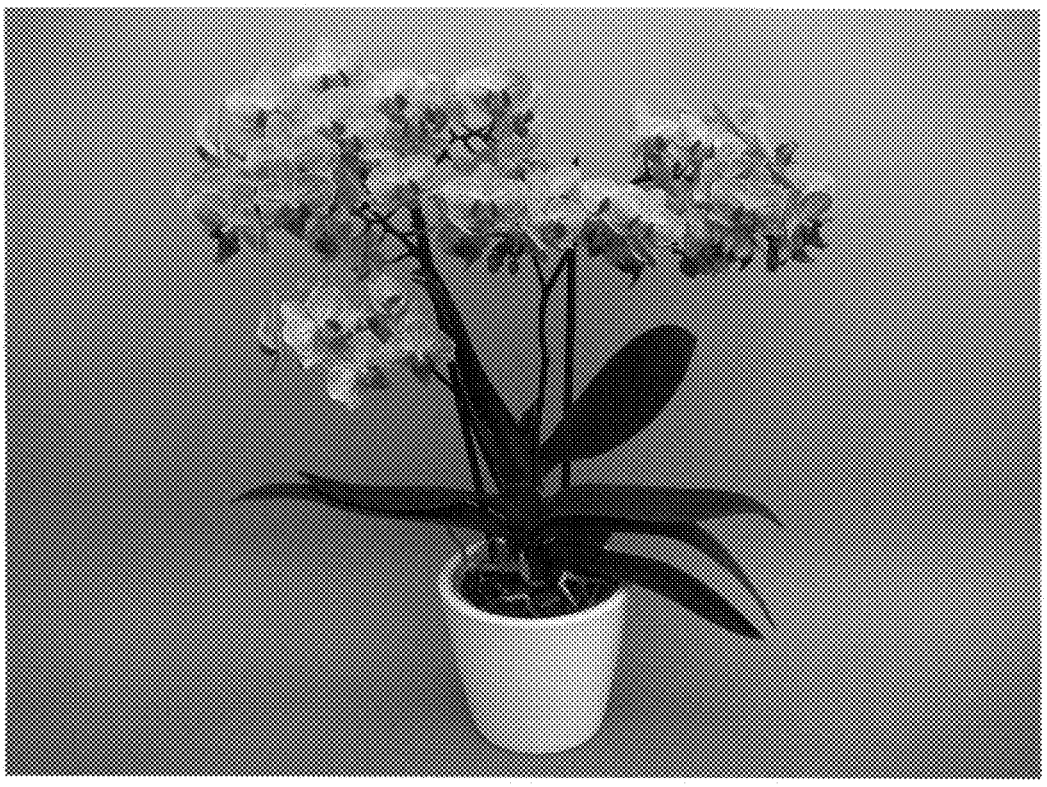
FIG. 1 shows the overall plant habit, including blooms, buds and foliage of 'PHALDONFI'.
Figure 2:
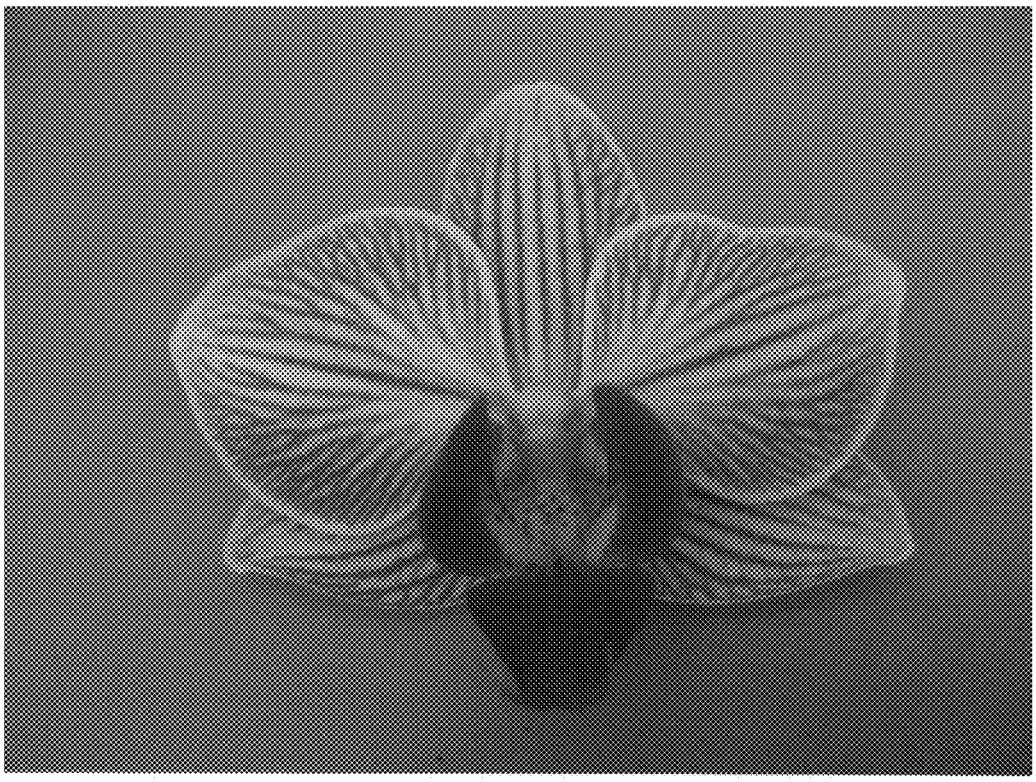
FIG. 2 shows a close-up of the flower of 'PHALDONFI'.
Figure 3:
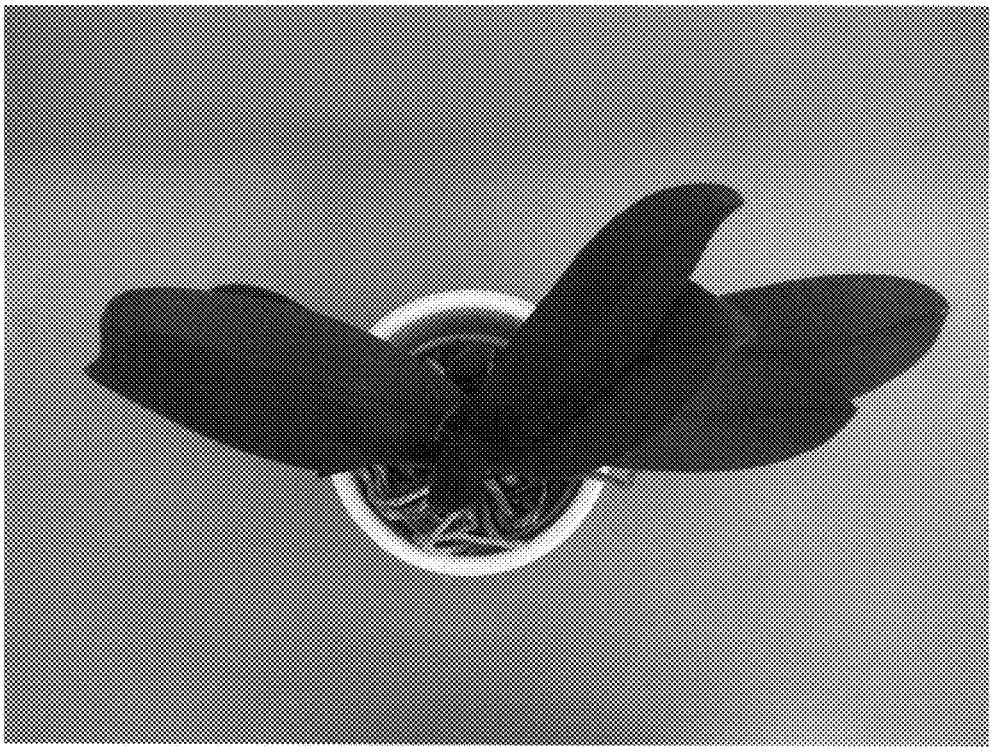
FIG. 3 shows a close-up of the leaves of 'PHALDONFI'.

The following detailed description sets forth the distinctive characteristics of 'PHALDONFI'. The data which define these characteristics were collected from asexual reproductions carried out in Bleiswijk, The Netherlands. The plant history was taken on 50-week old plants which were planted from tissue culture in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in April 2013. Color readings were taken under 4000 till 6000 lux natural light in the greenhouse. Color references are primarily to The R.H.S. Colour Chart of The Royal Horticultural Society of London (R.H.S.) (1995).

DETAILED BOTANICAL DESCRIPTION

Classification:
- *Family.*—Orchidaceae.
- *Botanical.*—*Phalaenopsis* hybrid.
- *Common name.*—*Phalaenopsis.*
- *Variety name.*—'PHALDONFI'.

Parentage:
- *Female parent.*—*Phalaenopsis* cultivar '01-0269' (unpatented).
- *Male parent.*—*Phalaenopsis* cultivar '01-1464' (unpatented).

Propagation:
- *Type.*—Meristem tissue culture.

Plant:
- *Crop time* (*time to produce a finished flowering plant*).—48 to 50 weeks for a 12 cm pot.
- *Growth habit of inflorescence.*—Standard type, green leaves and panicle.
- *Height* (*including pot, including inflorescence*).—40.0 cm to 50.0 cm.
- *Width* (*measured from leaf tips*).—36.0 cm to 40.0 cm.
- *Vigor.*—Strong to moderate.

Roots:
- *Root description.*—Grey-green-colored roots with light branching lateral roots having grey-green-colored root tips.

Leaves:
- *Mature leaves.*—Quantity per plant: 6 to 7 leaves are produced before flowering. Length (fully expanded): 18.0 cm to 20.0 cm. Width: 5.5 cm to 6.5 cm. Shape: Narrow oblong. Apex: Obtuse. Leaf blade angle with the petiole: Between 20 degrees and 40 degrees. Leaf margin: Entire. Color: Upper surface: RHS 137B. Lower surface: RHS 138B. Texture: Smooth. Thickness: 1.7 mm. Venation: Pattern: Parallel. Color of the midvein: Upper surface: RHS 137A. Lower surface: RHS 138A.

Peduncle:
- *Quantity per plant.*—2 to 3.
- *Number of flowers per peduncle.*—16 to 26.
- *Length.*—30.0 cm.
- *Diameter.*—About 0.5 cm.
- *Strength.*—Strong.
- *Aspect.*—Upright.
- *Texture.*—Smooth.
- *Color.*—Brown (RHS 200A).
- *Internode length.*—40.0 mm to 70.0 mm.

Inflorescence description:
- *Appearance.*—Upright to slightly pendant, panicle inflorescence with bilaterally symmetrical flowers that open in succession beginning with the lowermost flower.
- *Inflorescence size.*—Height (from base to tip): 50.0 mm to 60.0 mm. Diameter: 80.0 mm to 130.0 mm.
- *Flowering time.*—First flowers can be expected 10 to 11 months after planting in a 12 cm pot.
- *Flower.*—Height: 45.0 mm to 48.0 mm. Diameter: 52.0 mm to 56.0 mm. Depth of lip: 16.0 mm to 18.0 mm.
- *Flower longevity.*—On the plant: 13 to 15 weeks.
- *Fragrance.*—Absent.
- *Petals.*—Arrangement: Open. Shape: Semi-circular. Apex: Mucronate and symmetric. Margin: Slightly undulate. Length: 26.0 mm to 28.0 mm. Width: 25.0 mm to 27.0 mm. Color (when fully opened): Main color: Upper surface: Light pink (RHS 80D) with purple stripes (RHS 78A). Lower surface: Light pink (RHS 80D). At the base: Upper surface: Light pink (RHS 80D) with purple stripes (RHS 78A). Lower surface: Light pink (RHS 80D).
- *Dorsal sepal.*—Shape: Elliptic. Length: 26.0 mm to 28.0 mm. Width: 17.0 mm to 19.0 mm. Color (when fully opened): Main color: Upper surface: Light pink (RHS 80D) with purple stripes (RHS 78A). Lower surface: Light pink (RHS 80D). At the base: Upper surface: Light pink (RHS 80D) with purple stripes (RHS 78A). Lower surface: Light pink (RHS 80D).
- *Lateral sepals.*—Shape: Ovate Length: 17.0 mm to 19.0 mm. Width: 25.0 mm to 27.0 mm. Color (when fully opened): Main color: Upper surface: Light pink (RHS 80D) with purple stripes (RHS 78A) and greyed-green stripe towards the center (RHS 195D). Lower surface: Light pink (RHS 80D) with some RHS 160D. At the base: Upper surface: Light pink (RHS 80D) with purple stripes (RHS 78A) and greyed-green stripe towards the center (RHS 195D). Lower surface: Light pink (RHS 80D) with some RHS 160D.
- *Labellum* (*lip*).—Margin: Entire. Length: 15.0 mm to 18.0 mm. Width: 16.0 mm to 18.0 mm. Pubescence: Absent. Whiskers: Length: 3.0 mm to 4.0 mm. Color: Red-purple (RHS 71A).
- *Lateral lobe.*—Shape: type V (as described in the International Union for the Protection of New Varieties of Plants (UPOV) Test Guidelines for *Phalaenopsis*); spatulate. Color: Purple with white and yellow shade and purple spots (RHS 71A; 155C; 10C; 59A).

Length (from base to tip in widest part): 13.0 mm to 15.0 mm. Width (in widest part): 10.0 mm to 12.0 mm.

*Apical lobe*.—Shape: Obdeltoid. Color: Purple (RHS 71A). Length (from base to tip in widest part): 15.0 mm to 17.0 mm. Width (in widest part): 17.0 mm to 19.0 mm.

*Callus*.—Color: Yellow with purple spots (RHS 14B; 71A).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 9.0 mm to 10.0 mm. Diameter: 4.0 mm to 5.0 mm. Color: Purple (RHS 80B).

*Pollinia*.—Quantity: 2. Size: 1.0 mm to 1.1 mm. Color: Orange (RHS 26A).

*Ovary*.—Length: 8.0 mm to 9.0 mm. Diameter: 3.0 mm to 4.0 mm.

*Pedicel*.—Length: 26.0 mm to 30.0 mm. Diameter: 2.0 mm to 3.0 mm. Color: Greyed-green (RHS 195A) and purple (RHS 78C); toward the inflorescence the color is dark purple (RHS 79A); towards the flower the color is slightly lighter greyed-green (RHS 195B) and light purple (RHS 78C).

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALDONFI' differs from female parent '01-0269' (unpatented) in that 'PHALDONFI' has a lateral lobe that is white and slightly yellow towards the callus, whereas '01-0269' has a lateral lobe that is yellow towards the callus. Additionally, 'PHALDONFI' has a smaller callus, more narrow petals and a slightly lighter flower color than '01-0269'.

'PHALDONFI' differs from commercial variety 'CHUNLI' (unpatented) in that 'PHALDONFI' has short whiskers and a type I (per UPOV Test Guidelines for *Phalaenopsis*) curvature of the lateral lobe of the lip, whereas 'CHUNLI' has medium whiskers and a type II curvature of the lateral lobe of the lip. Additionally, 'PHALDONFI' has a darker yellow callus than 'CHUNLI'.

I claim:

1. A new and distinct variety of *Phalaenopsis* plant named 'PHALDONFI' as shown and described herein.

* * * * *